US012752031B2

(12) United States Patent
Vyas et al.

(10) Patent No.: US 12,752,031 B2
(45) Date of Patent: Oct. 6, 2026

(54) VOLATILE COMPOSITION DISPENSER WITH CARTRIDGE FOR MULTIPLE VOLATILE COMPOSITIONS

(71) Applicant: The Procter & Gamble Company, Cincinnati, OH (US)

(72) Inventors: Rahul Vyas, Singapore (SG); Bhavesh Rajwani, Singapore (SG); Gaurav Saini, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 218 days.

(21) Appl. No.: 18/810,842

(22) Filed: Aug. 21, 2024

(65) Prior Publication Data

US 2025/0065005 A1 Feb. 27, 2025

Related U.S. Application Data

(60) Provisional application No. 63/520,958, filed on Aug. 22, 2023.

(51) Int. Cl.
*A61L 9/12* (2006.01)

(52) U.S. Cl.
CPC ......... *A61L 9/125* (2013.01); *A61L 2209/131* (2013.01); *A61L 2209/133* (2013.01)

(58) Field of Classification Search
CPC ............... A61L 9/125; A61L 2209/131; A61L 2209/133
USPC ..................................................... 239/34–60
See application file for complete search history.

(56) References Cited

U.S. PATENT DOCUMENTS

| | | | | |
|---|---|---|---|---|
| 8,662,409 | B2 * | 3/2014 | Tasz | A61L 9/12 239/45 |
| 8,740,110 | B2 | 6/2014 | Gruenbacher | |
| 8,891,947 | B2 * | 11/2014 | Neumann | A61L 9/035 392/386 |
| 8,931,711 | B2 | 1/2015 | Gruenbacher | |
| 9,439,993 | B2 | 9/2016 | Gruenbacher | |
| 10,143,766 | B2 | 12/2018 | Gruenbacher | |

(Continued)

FOREIGN PATENT DOCUMENTS

| | | | |
|---|---|---|---|
| WO | 2011042232 | A1 | 4/2011 |
| WO | 2016088095 | A1 | 6/2016 |

OTHER PUBLICATIONS

PCT Search Report and Written Opinion for PCT/US2024/043023 dated Jan. 2, 2025, 12 pages.

*Primary Examiner* — Steven J Ganey
(74) *Attorney, Agent, or Firm* — Elizabeth A. Conklin; Carolyn S. Powell

(57) ABSTRACT

A cartridge for a volatile composition dispenser includes (a) a first chamber including a first chamber opening and containing a first volatile composition; (b) a second chamber including a second chamber opening and containing a second volatile composition, where the second chamber is fluidly isolated from the first chamber; (c) a first breathable membrane covering the first chamber opening and having a first evaporation region through which the first volatile composition can evaporate; and (d) a second breathable membrane covering the second chamber opening and having a second evaporation region through which the second volatile composition can evaporate. A ratio between a surface area of the first evaporation region to a surface area of the second evaporation region is in a range of 1:1.3 to 1:6.

20 Claims, 5 Drawing Sheets

(56) References Cited

U.S. PATENT DOCUMENTS

| | | | |
|---|---|---|---|
| 11,246,954 | B2 | 2/2022 | Fischer |
| 11,517,643 | B2 | 12/2022 | Gruenbacher et al. |
| 11,554,192 | B2 | 1/2023 | Govindan Radhakrishnan |
| 11,833,276 | B2 | 12/2023 | Govindan Radhakrishnan |
| 11,911,540 | B2 | 2/2024 | Gruenbacher et al. |
| 12,090,255 | B2 | 9/2024 | Gruenbacher |
| 2005/0199740 | A1* | 9/2005 | Harris, Jr. ........... A01M 31/008 239/34 |
| 2015/0028124 | A1 | 1/2015 | Freddi et al. |
| 2016/0354505 | A1 | 12/2016 | Gruenbacher |
| 2024/0058499 | A1 | 2/2024 | Govindan Radhakrishnan et al. |
| 2024/0148927 | A1 | 5/2024 | Gruenbacher et al. |
| 2024/0399013 | A1 | 12/2024 | Gruenbacher |

* cited by examiner

VOLATILE COMPOSITION DISPENSER WITH CARTRIDGE FOR MULTIPLE VOLATILE COMPOSITIONS

TECHNICAL FIELD

The present disclosure relates to the field of devices and systems for delivering a volatile composition and particularly relates to a volatile composition dispenser with a cartridge for multiple volatile compositions.

BACKGROUND

Systems for delivering volatile materials to the atmosphere are well known in the art, and include for example, insect repellents, air fresheners, malodour removal agents. Such systems function by evaporating a volatile material through a medium such as a permeable membrane into a space to deliver a variety of benefits such as air freshening or malodour removal or a combination thereof. Typically, the volatile composition is stored in a sealed cartridge that is opened or punctured to release the volatile composition to the air.

PCT Publication No. WO 98/16262 (hereinafter, "WO98/16262") describes a disposable air freshener dispenser device having a push-button actuator which can be manually operated to initiate the dispensing of air freshener composition into the atmosphere. The device of WO98/16262 has an air freshener medium within a cartridge, and a push button actuator which can be manually operated to rupture a foil covering the cartridge for initiating the dispensing of the air freshener into the atmosphere.

However, such dispenser is only adapted to dispense one kind of volatile composition or mixture of a plurality of volatile compositions. It cannot be used to separately cause evaporation of different volatile compositions. Furthermore, the evaporation profile of a single volatile composition can be undesirable over long periods of time. Volatile compositions such as perfumes are typically a mixture of different volatile materials, having different volatilities. When combined into a perfume composition in an air freshening product, the most volatile materials will typically evaporate first, while the least volatile materials may not evaporate at the start of a perfume product's life cycle because the vapor pressure of the most volatile materials may saturate the available evaporation airspace. This can result in a poorly balanced scent that is formed from a majority of top notes at the start of a product's life, and a majority of bottom notes at the end of a product's life.

SUMMARY

It has surprisingly been found that providing a product in which the more volatile and less volatile perfume components are separated and allowed to evaporate separately and with a controlled ratio of evaporative surface areas, may improve the release profile of all perfume components to provide an advantageously more balanced and pleasurable scent.

The present disclosure provides a cartridge for a volatile composition dispenser, comprising:

(a) a first chamber comprising a first chamber opening and containing a first volatile composition;

(b) a second chamber comprising a second chamber opening and containing a second volatile composition, where the second chamber is fluidly isolated from the first chamber;

(c) a first breathable membrane covering the first chamber opening and having a first evaporation region through which the first volatile composition can evaporate; and (d) a second breathable membrane covering the second chamber opening and having a second evaporation region through which the second volatile composition can evaporate;

wherein a ratio between a surface area of the first evaporation region to a surface area of the second evaporation region is in a range of 1:1.3 to 1:6.

The present disclosure also provides a volatile composition dispenser comprising:

the cartridge according to the present disclosure; and a housing defining an interior compartment within which the cartridge is disposed.

BRIEF DESCRIPTION OF THE DRAWINGS

While the specification concludes with the claims particularly pointing out and distinctly claiming examples of the present disclosure, it is believed that the present disclosure will be better understood from the following description taken in conjunction with the accompanying drawings in which:

DETAILED DESCRIPTION

Figure 1:
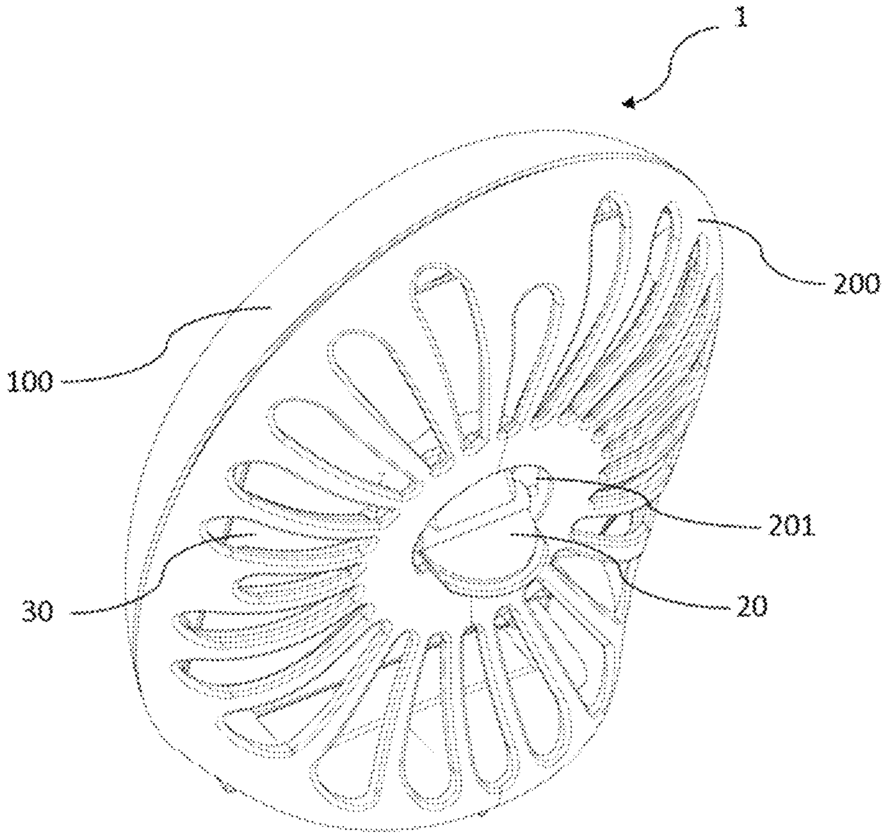
FIG. 1 is a rear perspective view of a volatile composition dispenser suitable for housing a cartridge according to examples.

The present disclosure provides a cartridge for a volatile composition dispenser, comprising:

(a) a first chamber comprising a first chamber opening and containing a first volatile composition;

(b) a second chamber comprising a second chamber opening and containing a second volatile composition, where the second chamber is fluidly isolated from the first chamber;

(c) a first breathable membrane covering the first chamber opening and having a first evaporation region through which the first volatile composition can evaporate; and (d) a second breathable membrane covering the second chamber opening and having a second evaporation region through which the second volatile composition can evaporate;

wherein a ratio between a surface area of the first evaporation region to a surface area of the second evaporation region is in a range of 1:1.3 to 1:6.

As used herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and examples of the present disclosure. In other words, the word "comprising" and synonyms thereof may be replaced by the phrase "consisting of" or the phrase "consists essentially of" or synonyms thereof and vice versa.

The phrase, "consists essentially of" and its pseudonyms may be interpreted herein to refer to a material where minor impurities may be present. For example, the material may be greater than or equal to 90% pure, such as greater than 95% pure, such as greater than 97% pure, such as greater than 99% pure, such as greater than 99.9% pure, such as greater than 99.99% pure, such as greater than 99.999% pure, such as 100% pure. When used herein, the term "substantially identical" is intended to refer to a dimension that is essentially identical, but for variations resulting from manufacturing tolerances. For example, the term may mean that a value varies by less than 5%, such as less than 2%, such as less than 1%, such as less than 0.5%, such as less than 0.05%, such as the dimension is essentially uniform.

As discussed herein, the first chamber and second chamber are fluidly isolated from each other. As used herein, when two components are described as being "fluidly isolated" from each other, this is to be understood as meaning that liquid may not flow between the two components which are fluidly isolated from each other. It may be possible for gases to flow between the two components. Therefore, the term "fluidly" in the phrase "fluidly isolated" as used herein refers only to liquids, and not to gases. In the context of the first chamber and the second chamber, liquid may not flow from the first chamber to the second chamber. The first and second evaporation regions may also be fluidly isolated from each other as described herein. In this context, the term "fluidly isolated" means that the passage of liquid from the first evaporation region to the second evaporation region is prevented, thereby preventing comingling of the first and second volatile compositions on the first and second evaporation regions. However, since both the first and second evaporation regions are exposed to the atmosphere, a skilled person will appreciate that gases may flow between the first and second evaporation regions.

The present disclosure relates to a cartridge for a volatile composition dispenser, which is suitable for the delivery of a volatile material to the atmosphere. The dispenser is suitable for purposes of providing fragrances, air fresheners, deodorizers, odour eliminators, malodour counteractants, insecticides, insect repellents, medicinal substances, disinfectants, sanitizers, mood enhancers, aromatherapy aids, or for any other purpose using a volatile material or a volatile composition that acts to condition, modify, or otherwise change the atmosphere or the environment. For the purposes of illustrating the present disclosure in detail, but without intending to limit the scope of the present disclosure, the cartridge of the present disclosure will be described in relation to a volatile composition dispenser for delivering a liquid composition containing perfume, perfume ingredients and/or perfume raw materials.

Various examples will now be described to provide an overall understanding of the principles of the structure, function, manufacture, and use of the apparatuses and methods disclosed herein. One or more examples of these examples are illustrated in the accompanying drawings. Those of ordinary skill in the art will understand that the apparatuses and methods specifically described herein and illustrated in the accompanying drawings are non-limiting example examples and that the scope of the various examples of the present disclosure are defined solely by the claims. The features illustrated or described in connection with one example may be combined with the features of other example examples. Such modifications and variations are intended to be included within the scope of the present disclosure.

FIG. 1 shows a rear perspective view of a volatile composition dispenser 1 that may be used with a cartridge 30 according to the present disclosure. The volatile composition dispenser 1 comprises a housing 10 having a front cover 100 and a rear frame 200, the front cover 100 and the rear frame 200 defining an interior compartment. The rear frame 200 is provided with a frame opening 201 located substantially in the centre of the rear frame 200. An activation member 20 is disposed within the frame opening 201 and is pivotable with respect to the rear frame 200 for enabling a user to activate the volatile composition dispenser 1, e.g. by actuating a rupture mechanism as described hereinbelow. A cartridge 30 containing a volatile composition is located within the housing 10.

Figure 2:
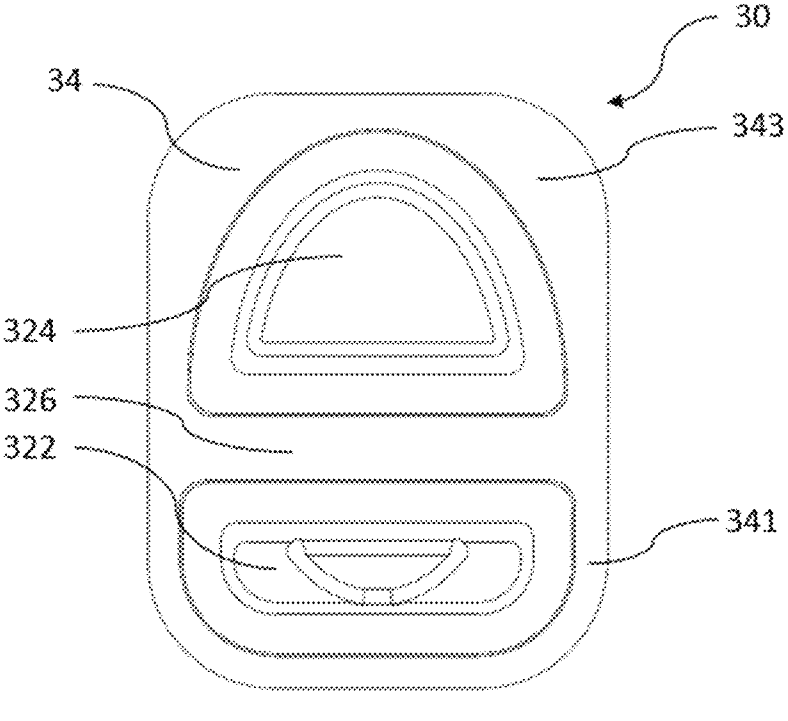
FIG. 2 is a rear view of a cartridge according to examples.
Figure 3:
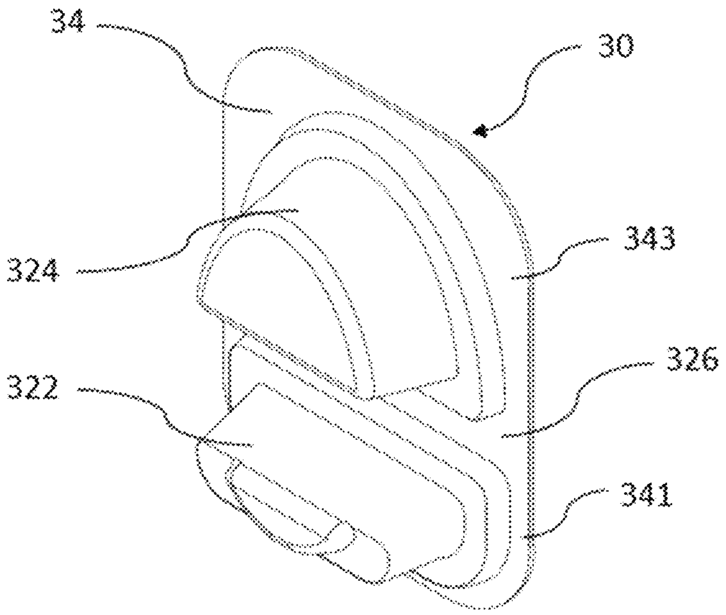
FIG. 3 is a perspective view of the cartridge shown in FIG. 2.
Figure 5:
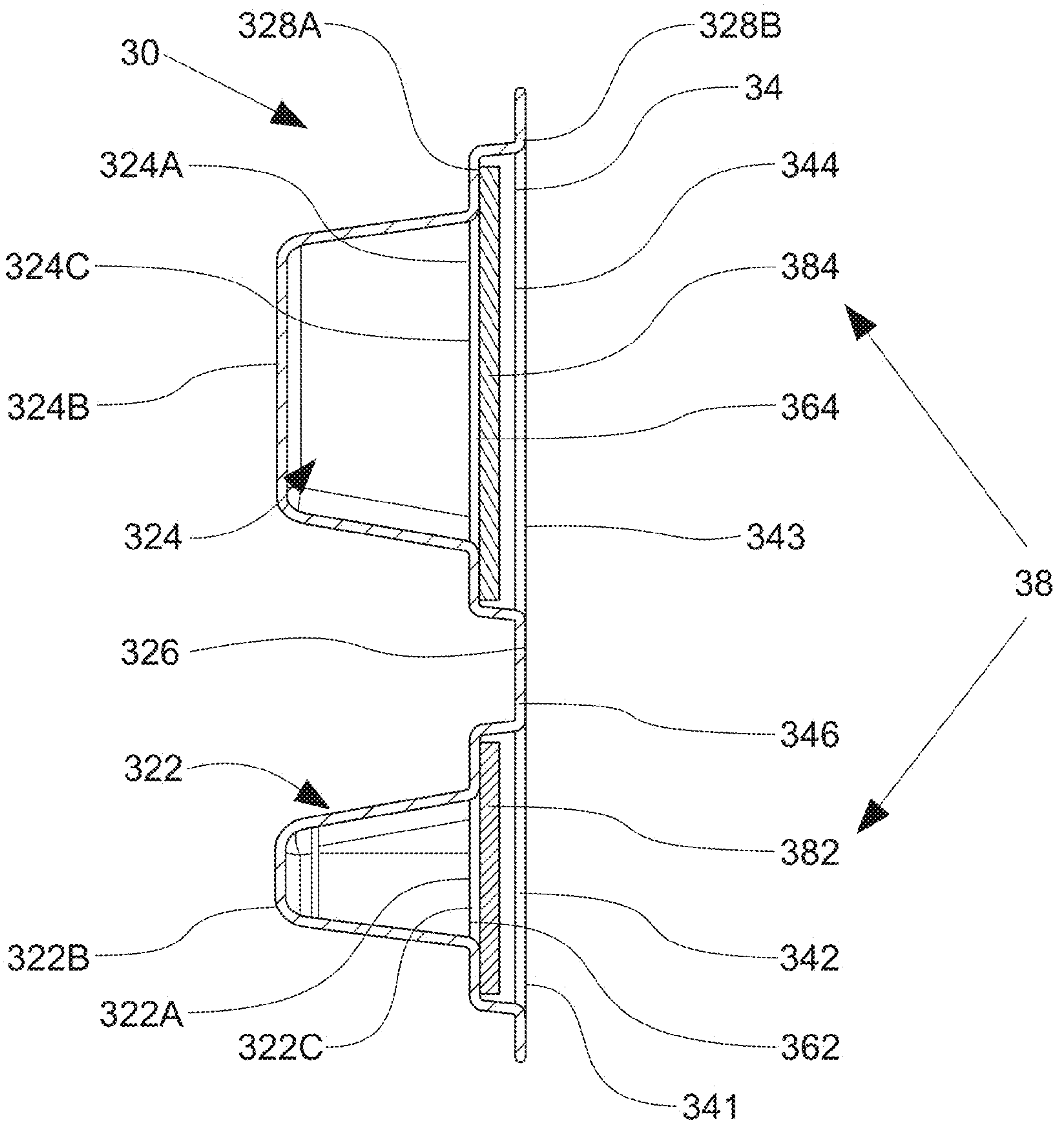
FIG. 5 is a side view of the cartridge shown in FIG. 2.

FIG. 2 is a rear view of a cartridge 30 according to an example of the present disclosure, FIG. 3 is a perspective view of the cartridge 30 and FIG. 5 is a side view of the cartridge 30. The cartridge 30 comprises:

(a) a first chamber 322 comprising a first chamber opening 322C and containing a first volatile composition;

(b) a second chamber 324 comprising a second chamber opening 324C and containing a second volatile composition, where the second chamber 324 is fluidly isolated from the first chamber 322;

(c) a first breathable membrane 341 covering the first chamber opening 322C and having a first evaporation region 342 through which the first volatile composition can evaporate; and (d) a second breathable membrane 343 covering the second chamber opening 324C and having a second evaporation region 344 through which the second volatile composition can evaporate;

wherein a ratio between a surface area of the first evaporation region 342 to a surface area of the second evaporation region 344 is in a range of 1:1.3 to 1:6.

According to the example as shown in FIGS. 2 and 3, the first chamber 322 can be arranged side by side (whether in a vertical or horizontal manner) with the second chamber 324, in which the first chamber forms together with the second chamber a defined shape of cross-section, such as an oval. It can be easily anticipated by the skilled in the art that the first chamber 322 and the second chamber 324 could have other shape of cross-section, for example, a circle, a square, a rectangle, a polygon, etc.

According to some examples of the present disclosure, the first chamber 322 can be fluidly isolated from the second chamber 324, such that the volatile composition in one of the first and second chambers cannot diffuse/migrate to the other chamber. For example, the first volatile composition in the first chamber 322 will not be mixed with the second volatile composition in the second chamber 324. In one example as shown, the first chamber 322 is separated from the second chamber 324 by a chamber separating section 326 located between the first chamber 322 and the second chamber 324. In this case, the first chamber 322 can be connected to but fluidly isolated from the second chamber 324 by the chamber separating section 326.

The cartridge 30 comprises a first breathable membrane 341 and a second breathable membrane 343. The first and second breathable membranes 341, 343 may form part of a unitary sheet 34 as shown in FIGS. 2 and 3, which may be configured to cover the first and second chambers 322, 324, as shown in FIGS. 2 and 3.

Figure 4:
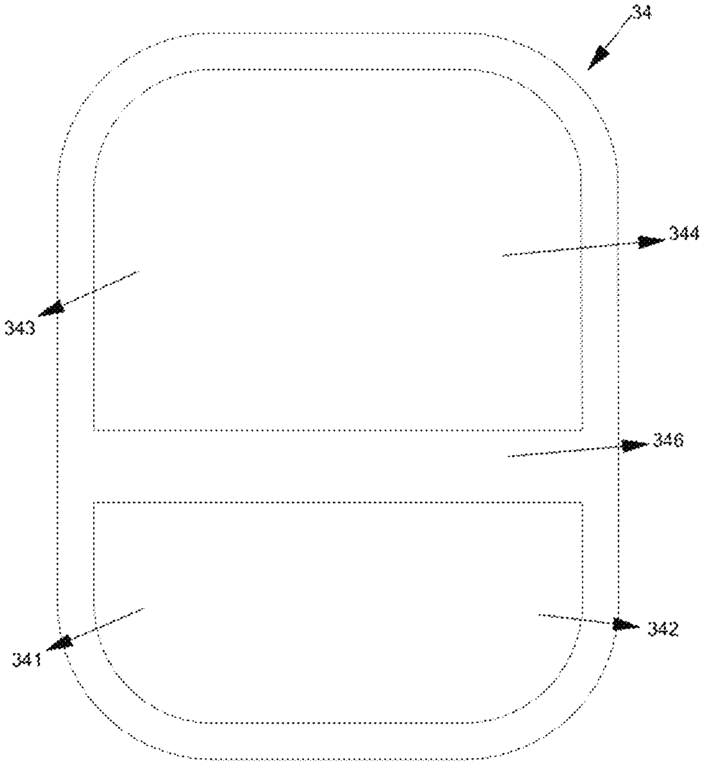
FIG. 4 is a front view of a cartridge according to examples.

FIG. 4 is a front view of a sheet 34. The sheet 34 can comprise a first breathable membrane 341 covering the first chamber opening 322C and having a first evaporation region 342 through which the first volatile composition in the first chamber 322 can evaporate, and a second breathable membrane 343 covering the second chamber opening 324C and having a second evaporation region 344 through which the second volatile composition in the second chamber 324 can evaporate. In the example depicted in FIG. 4, the first evaporation region 342 corresponds to the cross-section of, and covers, the first chamber 322, and the second evaporation region 344 corresponds to the cross-section of, and covers, the second chamber 324. The first evaporation region 342 can be fluidly isolated from the second evaporation region 344. This may be achieved by a sealing region 346 that prevents the passage of liquid perfume between the first and second evaporation regions 342, 344, as described herein.

Thus, cartridge 30 can comprise a sealing region 346 located between the first evaporation region 342 and the second evaporation region 344, and configured to fluidly isolate (i.e. prevent the passage of liquid between) the first evaporation region 342 and the second evaporation region 344 from each other. As depicted in FIG. 5, the sealing region 346 may be the same as the chamber separating section 326, for example the sealing region 346 may be an impermeable piece of material that forms the chamber separating section 326. Thus, the sealing region 346 may represent a gap between the first and second 324, 344 evaporation regions. In an alternative configuration, the sealing region 346 may form part of the sheet 34, and may be bonded to the chamber separating section 326. In such cases, the sealing region 346 may be formed from an impermeable material on or impregnated into an appropriate part of the sheet 34 to prevent lateral flow of fluid along the sheet 34. The sealing region 346 prevents mixing of the first and second volatile compositions as they evaporate from the first and second evaporation regions 342, 344. At the same time, the separating section 326 may separate the first and second chambers 322, 324 from each other.

FIG. 5 is a side view of the cartridge 30 shown in FIG. 2. As shown, the first chamber 322 is arranged side by side with the second chamber 324. The first chamber 322 comprises a top portion 322A defining the first chamber opening 322C and a bottom portion 322B being enclosed. Likewise, the second chamber 324 comprises a top portion 324A defining the second chamber opening 324C and a bottom portion 324B being enclosed. The first chamber 322 and the second chamber 324 could be formed through punching a sheet. After punching, a first step 328A could be formed around the first chamber opening 322C and the second chamber opening 324C, and further a second step 328B could be formed as an extension of the first step 328B. In this case, the chamber separating section 326 could be positioned on the second step 328B between the first chamber 322 and the second chamber 324, and the edge of the sheet 34 could be bonded onto the second step 328B. In this case, the first breathable membrane 341 could be substantially coplanar with the second breathable membrane 343, and thus the first evaporation region 342 could be substantially coplanar with the second evaporation region 344.

As used herein, "substantially coplanar" means that two components are in the same plane, or are only marginally offset from the same plane. For example, the two components may be offset by a distance of less than 15 mm, less than 10 mm, less than 9 mm, less than 8 mm, less than 7 mm, less than 6 mm, or less than 5 mm. Alternatively, the second component may be offset from a first component by an angle of less than 30°, less than 25°, less than 20°, less than 15°, less than 10° or less than 5°.

According to some examples of the present disclosure, as shown in FIG. 5, the top portion 322A of the first chamber 322 could be substantially coplanar with the top portion 324A of the second chamber 324, as a result of punching a sheet to form the first and second chambers 322, 324, such that the first chamber opening 322C could be substantially coplanar with the second chamber opening 324C. Further, the bottom portion 322B of the first chamber 322 could also be substantially coplanar with the bottom portion 324B of the second chamber 324. That is, the height of the first chamber 322 could be the same as the height of the second chamber 324. Multiple chambers are configured to be substantially co-planar with each other, with similar total heights and steps to ensure that the components associated with different chambers could be levelled with each other. This will advantageously simplify the manufacturing process of the cartridge of the present disclosure.

According to some examples of the present disclosure, as shown in FIG. 5, the cartridge 30 may comprise a first rupturable impermeable substrate 362 which may be disposed over the first chamber opening 322C and be configured to seal the first chamber 322. The cartridge 30 may also comprise a second rupturable impermeable substrate 364 which could be disposed over the second chamber opening 324C and also could be configured to seal the second chamber 324. The first rupturable impermeable substrate 362 has an unruptured state in which the first rupturable impermeable substrate 362 prevents contact between the first volatile composition and the first breathable membrane/first evaporation region, thereby preventing evaporation of the first volatile composition. The first rupturable impermeable substrate also has a ruptured state, which allows contact between the first volatile composition and the first breathable membrane 341/first evaporation region 342, thereby allowing evaporation of the first volatile composition. The second rupturable impermeable substrate 364 has unruptured and ruptured states which allow and prevent contact between the second volatile composition and second breathable membrane 343/second evaporation region 344 in an analogous manner.

The first rupturable impermeable substrate 362 is provided at the first chamber opening 322C of the first chamber 322 to cover and seal the first chamber opening 322C, but is itself enclosed by the first breathable membrane 341. In this way, the first rupturable impermeable substrate 362 may be located between the first volatile composition and the first breathable membrane 341. The second rupturable impermeable substrate 364 is provided at the second chamber opening 324C of the second chamber 324 to cover and seal the second chamber opening 324C, but is itself enclosed by the second breathable membrane 343. In this way, the second rupturable impermeable substrate 364 may be located between the second volatile composition and the second breathable membrane 343. The edges of the first rupturable impermeable substrate 362 and the second rupturable impermeable substrate 364 could be bonded onto the first step 328A. Alternatively, and not shown in FIG. 5, the first rupturable impermeable substrate 362 and the second rupturable impermeable substrate 364 could be formed integrally. In this case, the first rupturable impermeable substrate 362 and the second rupturable impermeable substrate 364 could be bonded onto the first step 328A and the chamber separating section 326, or form part of the chamber separating section 326. The sealing region 346 could be bonded to the rupturable impermeable substrate at the chamber separating section 326.

According to some examples of the present disclosure, as shown in FIG. 5, the first rupturable impermeable substrate 362 could be disposed between the first chamber 322 and the first breathable membrane 341, and the second rupturable impermeable substrate 364 could be disposed between the second chamber 324 and the second breathable membrane 343. In the unruptured state of the first rupturable impermeable substrate 362, the first rupturable impermeable substrate 362 prevents contact of the first volatile composition with the first breathable membrane 341, and in the ruptured state of the first rupturable impermeable substrate 362, the first rupturable impermeable substrate 362 allows contact of the first volatile composition with the first breathable membrane 341. Likewise, in the unruptured state of the second rupturable impermeable substrate 364, the second rupturable impermeable substrate 364 prevents contact of the second volatile composition with the second breathable membrane 343, and in the ruptured state of the second rupturable impermeable substrate 364, the second rupturable impermeable substrate 364 allows contact of the second volatile composition with the second breathable membrane 343.

Figure 6:
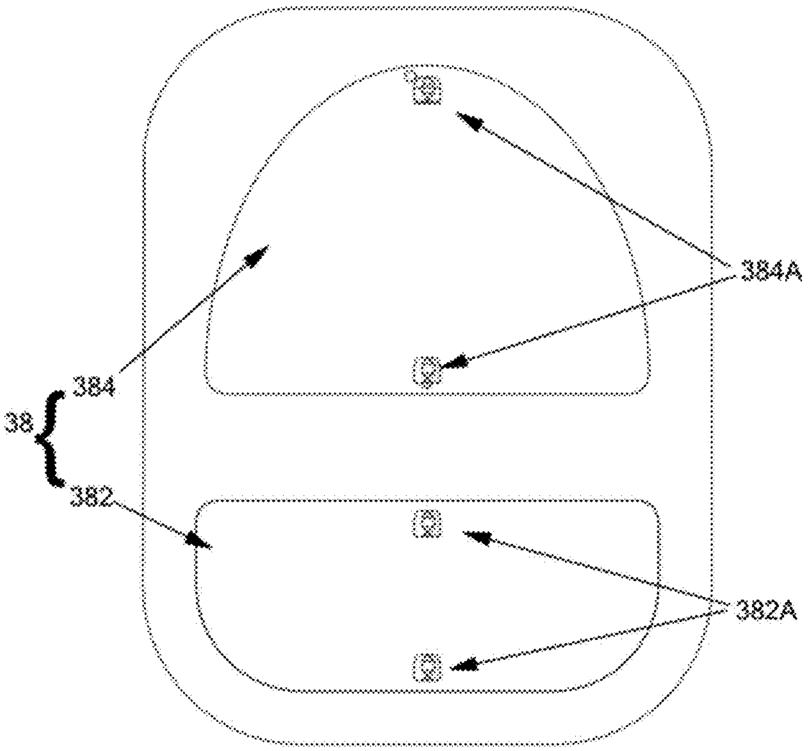
FIG. 6 is a front view of a rupture mechanism suitable for use in examples.

According to some examples of the present disclosure, as shown in FIGS. 5 and 6, the cartridge 30 could comprise a rupture mechanism 38. FIG. 6 is a front view of the rupture mechanism 38 of the cartridge 30 according to an example. The rupture mechanism 38 could be sandwiched between the first and second rupturable impermeable substrates 362, 364 and the first and second breathable membranes 341, 342, and configured to, upon activation, cause rupture of the first and second rupturable impermeable substrates 362, 364. In one example, the first and second rupturable impermeable substrates 362, 364 could be pierced by the rupture mechanism 38 simultaneously.

The rupture mechanism 38 could comprise at least a first rupture element 382 configured to, upon activation, pierce the first rupturable impermeable substrate 362 such that the first rupturable impermeable substrate 362 could be transitioned from the unruptured state to the ruptured state thereof and a second rupture element 384 configured to, upon activation, pierce the second rupturable impermeable substrate 364 such that the second rupturable impermeable substrate 364 could be transitioned from the unruptured state to the ruptured state thereof. According to some examples of the present disclosure, the rupture mechanism 38 could be configured to, upon activation, cause rupture of the first and second rupturable impermeable substrates 362, 364, and optionally the rupture mechanism 38 could be configured to, upon activation, cause simultaneous rupture of the first and second rupturable impermeable substrates 362, 364. For example, upon activation, the first rupture element 382 may cause rupture of the first rupturable impermeable substrate 362, and at the same time the second rupture element 384 may cause rupture of the second rupturable impermeable substrate 364.

According to some examples of the present disclosure, as shown in FIG. 5, the first rupture element 382 could be sandwiched between the first rupturable impermeable substrate 362 and the first evaporation region 342 of the first breathable membrane 341, and the second rupture element 384 could be sandwiched between the second rupturable impermeable substrate 364 and the second evaporation region 344 of the second breathable membrane 343. As shown in FIG. 6, the first rupture element 382 and the second rupture element 384 could be formed separately from each other. The edge of the first rupture element 382 could be positioned on the first step 328A, and the edge of the second rupture element 384 could be also positioned on the first step 328A, as shown in FIG. 5.

According to some examples of the present disclosure, the first rupture element 382 could be provided with at least one rupture pin 382A configured to pierce the first rupturable impermeable substrate 362, and the second rupture element 384 could be provided with at least one rupture pin 384A configured to pierce the second rupturable impermeable substrate 364. In the example as shown in FIG. 6, two rupture pins 382A and two rupture pins 384A are provided. However, it can be easily anticipated by the skilled in the art that the number of the rupture pins could be other than as shown, for example, one or more than two rupture pins. Further, the location of the rupture pins 382A, 384A could be selected as needed.

The first rupture element 382 under actuation will pierce the first rupturable impermeable substrate 362 by its rupture pin 382A, so as to form a through-hole in the first rupturable impermeable substrate 362. The first volatile composition may then flow through the through-hole and contact the first evaporation region 342 of the first breathable membrane 341. The first volatile composition may be wicked into the first evaporation region 342 of the first breathable membrane 341, therefore allowing evaporation of the first volatile composition to the surrounding environment.

Likewise, the second rupture element 384 under actuation will pierce the second rupturable impermeable substrate 364 by its rupture pin 384A, so as to form a through-hole in the second rupturable impermeable substrate 364. The second volatile composition may then flow through the through-hole and contact the second evaporation region 344 of the first breathable membrane 343. The second volatile composition may then be wicked into the second evaporation region 344 of the second breathable membrane 343, therefore allowing evaporation of the second volatile composition to the surrounding environment.

It can be seen that due to the chamber separating section 326 and the sealing region 346 of the sheet 34, the first volatile composition cannot be mixed with the second volatile composition prior to evaporation out of the cartridge 30. After the first volatile composition and the second volatile composition are evaporated outside of the first and second breathable membranes 341, 343, they may mix to form a desired scent.

Figure 7:
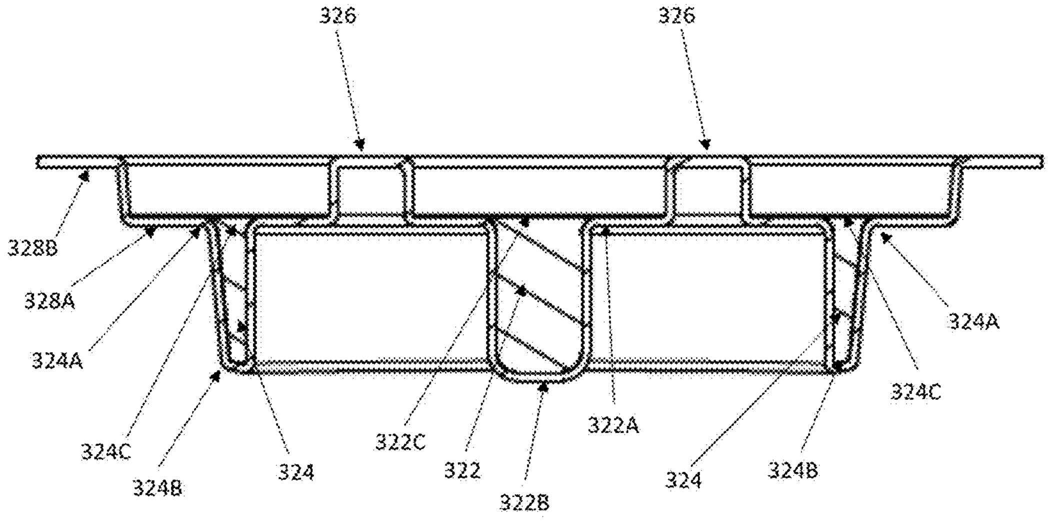
FIG. 7 is a cross-section view of a cartridge according to examples.
Figure 8:
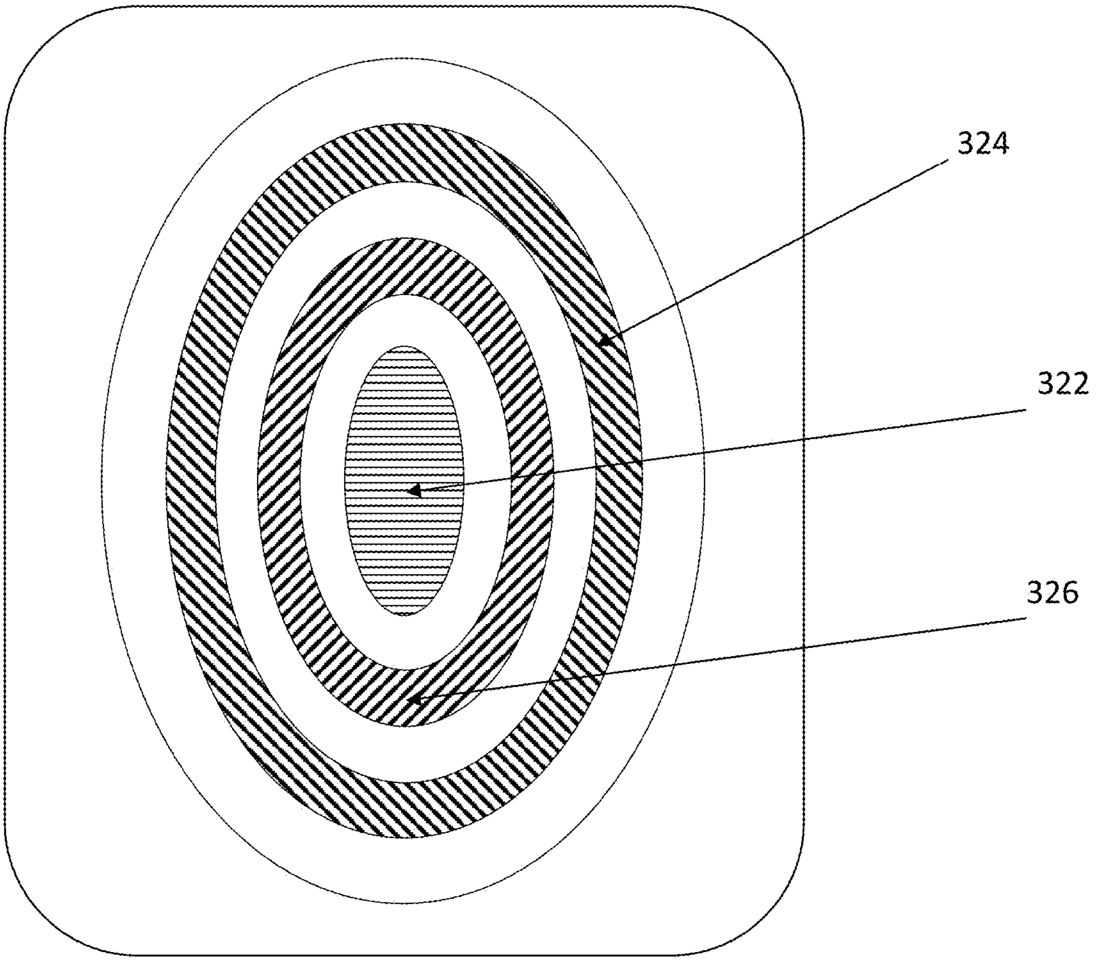
FIG. 8 is a front view of a cartridge shown in FIG. 7.

FIG. 7 is a cross-section view of the cartridge 30 according to another example. FIG. 8 is a front view of the cartridge 30 shown in FIG. 7. In this example, the first chamber 322 is partially surrounded by the second chamber 324 (i.e. in two dimensions), in which the first chamber 322 and the second chamber 324 both have an oval shape cross-section. Preferably, the first chamber is surrounded by the second chamber in only two dimensions, such that both chambers may have chamber openings, and corresponding breathable membranes/evaporation regions that are substantially coplanar. It can be easily anticipated by the skilled in the art that the first chamber 322 and the second chamber 324 could have other shape of cross-section, for example, a circle, a square, a rectangle, a polygon, etc. According to another example, the first chamber 322 can also be configured to surround the second chamber 324, in which the first chamber 322 and the second chamber 324 are both in the form of oval shape of cross-section.

As described above, upon the actuation of the rupture mechanism 38 and thus the first and second rupturable impermeable substrates 362, 364 being pierced, the first and second volatile compositions could be evaporated from the first and second chambers 322, 324 through the first and second evaporation regions 342, 344 of the first and second breathable membranes 341, 343 respectively, and then mixed with each other to form a scent. Different scents may be achieved through adjusting the volume ratio, and evaporation rates, of the first and second volatile compositions.

As known, different volatile compositions have different evaporation rates. Some volatile composition may have a higher evaporation rate, and the other may have a lower evaporation rate. For example, when exposed to identical conditions, the evaporation rate of the first volatile composition may be higher than that of the second volatile composition. The evaporation rates of the compositions from the cartridge of the present disclosure may be equalised, at least to some degree, by controlling the area of the first evaporation region 342 to be smaller than that of the second evaporation region 344. The relative increasing of the evaporation rate for the less volatile composition may allow for the creation of a more pleasing scent or aroma in the vicinity of the cartridge.

For example, in the case that the evaporation rate of the first volatile composition in the first chamber 322 at standard temperature and pressure is higher than the evaporation rate of the second volatile composition in the second chamber 324 at standard temperature and pressure, the surface area of the first evaporation region 342 for the evaporation of the first volatile composition can be smaller than the surface area of the second evaporation region 344 for the second volatile composition. Therefore, the volume of the (more volatile) first volatile composition evaporated through the first evaporation region 342 will be reduced, relatively, and the volume of the (less volatile) second volatile composition evaporated through the second evaporation region 344 will be increased, relatively.

The relative evaporation rates of the first and second volatile compositions, may be changed or adjusted by controlling setting the ratio between the surface areas of the first and second evaporation regions 342, 344. According to some examples of the present disclosure, the ratio between the surface area of the first evaporation region 342 and the surface area of the second evaporation region 344 may be from 1:1.3 to 1:6, preferably from 1:1.4 to 1:5, more preferably from 1:1.5 to 1:4, even more preferably from 1:1.6 to 1:3 and most preferably from 1:1.6 to 1:2. By varying the surface area ratio between the first and second evaporation regions 342, 344 while keeping the total surface area of the sheet 34 constant, it is possible to obtain the desired blend of the first and second volatile compositions, and thus the desired scent. This may result in a more 'balanced' scent character which consumers find more desirable.

By controlling the ratio of the evaporation regions, it is advantageously simple to control the rate at which the first and second volatile compositions evaporate. In particular, the examples of the present disclosure avoid the need for specific evaporation retardant barriers to be used to slow evaporation of a faster-evaporating material, and enables the same membrane material to be used over each of the first and second volatile compositions. The examples of the present disclosure also enable an advantageously simple and compact design, with the first and second evaporation regions being able to have a side by side configuration.

The first and second volatile compositions may have different evaporation rates from the cartridge 30. Therefore, the volume of the first volatile composition to be evaporated may be different from the volume of the second volatile composition to be evaporated. According to some examples of the present disclosure, the volume of the first chamber 322 can be different from the second chamber 324, so as to allow perfume evaporation over product life to be more balanced, as quantified by mg of perfume released per unit time. In particular, the ratio between the volume of the first chamber 322 and the volume of the second chamber 324 may be in a range of 1:1 to 1:6, preferably in a range of 1:1 to 1:2, more preferably in a range of 1:1 to 1:1.75, and most preferably about 1:1.4. By regulating and controlling the volume ratio between the first chamber 322 and the second chamber 324, it is possible, for example, to have the first volatile composition and the second volatile composition depleted substantially simultaneously during the life of the cartridge 30 so that it is possible to obtain always the desired blend of the first and second volatile compositions, and thus the desired scent during the life of the cartridge 30.

Since the volatile compositions are evaporated through the first and second breathable membranes 341, 343, the evaporation of the volatile composition is also influenced by the parameters of the first and second breathable membranes 341, 343, for example, the pore size etc. According to some examples of the present disclosure, the first evaporation region 342 has a first pore size and the second evaporation region 344 has a second pore size which can be different from or the same as the first pore size. In particular, pore sizes of the first and second breathable membranes 341, 343 may be selected to increase or decrease the evaporation rates of the first and second volatile materials, as may be desired.

The volatile composition dispenser 1 useful with the cartridge 30 of the present disclosure may have a small form factor such as a form factor similar to a computer mouse so as for ergonomic fit in the hand of the user and ease of use. The internal components of the cartridge 30 may be characterized as follows. For example, dimensions of the cartridge 30 may be configured to hold about 1 ml to about 50 ml of a liquid volatile composition. Alternatively, the reservoir may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of a liquid volatile composition. Further, a shape of the cartridge 30 may be configured to correspond to a shape of the opening of the front cover 100. For example, the cartridge 30 may define a substantially elliptical or oval shape and its width to length ratio may be about 1:2 to 1:2.5.

The rupturable impermeable substrates 342, 344 could be made of any material that ruptures with applied force, with or without the presence of an element to aid in such rupture. Because the rupturable impermeable substrates 342, 344 are intended to contain a volatile material while in storage, it may be made from any barrier material that prevents evaporation of the volatile material prior to its intended use. Such materials may be impermeable to vapours and liquids. Suitable barrier materials for the rupturable impermeable substrates 342, 344 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminium foil, a polyurethane primer, and 15 g/m$^2$ polyethylene coating (Lidfoil 118-0092), available from Alcan Packaging. Suitable polymeric films include polyethylene terephthalate (PET) films, acrylonitrile copolymer barrier films such as those sold under the tradename Barex® by INOES, ethylene vinyl alcohol, and combinations thereof. It is also contemplated that coated barrier films may be utilized as rupturable impermeable substrates 342, 344. Such coated barrier films include metallized PET, metalized polypropylene, silica, or alumina coated film may be used. Any barrier material, whether coated or uncoated, may be used alone and or in combination with other barrier materials.

The rupture elements 382, 384 could be injection, compression, or pressure molded using a polyolefin, such as polyethylene or polypropylene; polyester; or other plastics known to be suitable for molding. The rupture elements 382, 384 could also be made by thermoforming with a discrete cutting step to remove parts not wanted.

The first and second breathable membranes 341, 343 may have any appropriate average pore size, for example from about 0.01 to about 0.2 microns, alternatively from about 0.02 to about 0.18 microns, alternatively about 0.03 to about 0.17 microns, alternatively about 0.04 to about 0.16 microns. The first and second breathable membranes 341, 343 may have an average pore size (e.g. volume average pore diameter) of from about 0.065 to about 0.15 microns. Further, the first and second breathable membranes 341, 343 may be filled with any suitable filler and plasticizer known in the art. Fillers may include finely divided silica, clays, zeolites, carbonates, charcoals, and mixtures thereof. The microporous first and second breathable membranes 341, 343 may be filled with about 30% to about 80%, by total weight, of silica. A thickness of the first and second breathable membranes 341, 343 may be about 0.01 mm to about 1 mm, alternatively between about 0.1 mm to 0.4 mm, alternatively about 0.15 mm to about 0.35 mm, alternatively about 0.25 mm.

Still further, an evaporative surface area of the first and second breathable membranes 341, 343 may be about 2 $cm^2$ to about 100 $cm^2$, alternatively about 2 $cm^2$ to about 25 $cm^2$, alternatively about 10 $cm^2$ to about 50 $cm^2$, alternatively about 10 $cm^2$ to about 45 $cm^2$, alternatively about 10 $cm^2$ to about 35 $cm^2$, alternatively about 15 $cm^2$ to about 40 $cm^2$, alternatively about 15 $cm^2$ to about 35 $cm^2$, alternatively about 20 $cm^2$ to about 35 $cm^2$, alternatively about 30 $cm^2$ to about 35 $cm^2$, alternatively about 35 $cm^2$. Accordingly, the rear frame 200 may be sized and shaped to fit the evaporative surface area of the first and second breathable membranes 341, 343.

Suitable microporous membranes for the present disclosure include polyethylene, such as microporous, ultra-high molecular weight polyethylene (UHMWPE). As used herein, UHMWPE refers to polyethylene having a molecular mass of from about 3.5 million to 7.5 million amu. The UHMWPE may optionally be filled with silica as described in U.S. Pat. No. 7,498,369. Suitable UHMWPE microporous membranes include Daramic™ V5, available from Daramic, Solupor®, available from DSM (Netherlands), DuroForce® from Microporous™ and Teslin™ available from PPG Industries, and combinations thereof.

While the examples of the present disclosure are discussed hereinabove in relation to a two-chamber cartridge containing two separate volatile compositions, a person skilled in the art will understand that the concepts and examples disclosed herein may be applied to a cartridge having more than two chambers, e.g. having three or four chambers.

Thus, the present disclosure also provides a cartridge further comprising:

a third chamber comprising a third chamber opening and containing a third volatile composition;

a third breathable membrane covering the third chamber opening and having a third evaporation region through which the third volatile composition can evaporate.

All features of the present disclosure described herein may be applied to a cartridge having more than two chambers in an analogous manner. For example a cartridge further comprising a third chamber having equivalent features to the first and second chamber may have any of the following properties:

a) the cartridge may also comprise a second sealing region fluidly isolating (i.e. preventing the passage of liquid between) the third evaporation region from the first and second evaporation regions;

b) any part of the third chamber may be substantially coplanar with a corresponding part of the first and/or second chambers (e.g. a top portion, a bottom portion, a chamber opening);

c) the third chamber may be arranged side by side with the first and/or second chambers;

d) the third evaporation region may be substantially coplanar with the first and/or second evaporation regions;

e) the third chamber may partially surround, or be partially surrounded by, the first and/or second chambers (e.g. in two dimensions);

f) the cartridge may comprise a third rupturable impermeable substrate in an analogous manner to the first and second rupturable impermeable substrates described herein, which third rupturable impermeable substrate may be activated by a rupture mechanism to cause sequential or simultaneous rupturing of the third rupturable impermeable substrate with the first and/or second rupturable impermeable substrates;

g) the third volatile composition may have any property described herein in relation to the first and second volatile composition; and h) a ratio of the surface areas and/or chamber volumes for the first:second:third chamber/evaporative regions may be from about 1:2:4 to about 1:6:6.

A volatile material or composition suitable for use in the cartridge 30 may be configured to condition, modify, or otherwise change the atmosphere and may include compositions suitable for the purposes of providing fragrances, air fresheners, deodorizers, odor eliminators, malodor counteractants, insecticides, insect repellents, medicinal substances, disinfectants, sanitizers, mood enhancers, and aromatherapy aids. A list of the suitable volatile materials is shown in Table 1 below.

TABLE 1

| Purpose | Volatile Material |
|---|---|
| Providing fragrances | Perfume oil, volatile essential oils, volatile organic compound, synthetically or naturally formed materials.<br>Examples of appropriate oils include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. |

TABLE 1-continued

| Purpose | Volatile Material |
|---|---|
| | Suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, eugenol acetate, evenyl, and the like. Examples of appropriate synthetic materials include, but are not limited to: cyclic ethylene dodecanedioate, 4-tertiary butyl cyclohexyl acetate or vertenex ™, allyl amyl glycolate, allyl caproate, allyl cyclohexane propionate, allyl heptanoate, amber xtreme, ambrox, isoamyl acetate, isoamyl propionate, anethole usp, benzyl acetate, benzyl propionate, cis-3-hexen-1-ol, beta naphthol methyl ether or nerolin, caramel furanone, caryophyllene extra, cinnamalva ™ or Cinnamyl Nitrile, cinnamyl acetate, cinnamyl nitrile, cis-3-hexenyl butyrate, cis-3-hexenyl acetate, cis-3-hexenyl alpha methyl butyrate, cis-6-nonen-1-ol, citrathal or citral diethyl acetal, citronellol, citronellyl acetate, citronellyl butyrate, clonal or dodecane nitrile, coranol or 2,2-dimethyl cyclohexanepropanol, coumarin, cumin nitrile, cuminic alcohol, tricyclodecenyl isobutirate or cyclabute, cyclohexyl ethyl acetate, dihydromyrcenol, dimethyl anthranilate, dimethyl benzyl carbinyl acetate, dimethyl-2 6-heptan-2-ol or freesiol, sandal pentenol or ebanol, ethyl-2-methyl pentanoate, ethyl acetoacetate, ethyl linalool, ethyl maltol, ethyl phenyl glycidate, ethyl vanillin, ethyl-2-methyl butyrate, eucalyptol, eugenol, flor acetate, ozone propanal or floralozone, fructalate ™ or raspberry dicarboxylate, geraniol or trans-3,7-dimethyl-2,7-octadien-1-ol, grisalva ™ or amber furan, habanolide ™ or (E)-12-musk decenone, helvetolide ™ or musk propanoate, hexyl acetate, hexyl-2-methyl butyrate, indocolore ™ or 1-phenylvinyl acetate, iso bornyl acetate, iso eugenyl acetate, iso propyl myristate, isoamyl butyrate, isoeugenol, koumalactone ™ or dihydromint lactone, laevo trisandol or sandranol, lemonile ™ or homogeranyl nitrile, levistamel ™ or mesitene lactone, linalool, linalyl acetate, linalyl iso butyrate, lymolene or dihydromyrcenol, menthol, methyl dioxolan or fructone ™, methyl iso butenyl tetrahydro pyran, methyl pamplemousse ™ or grapefruit acetal, methyl phenyl carbinyl acetate or styrallyl acetate, methyl salicylate, montaverdi ™ or green cyclopropionate, mugetanol ™ or muguet ethanol, neocaspirene, neofolione or melon nonenoate nerolidol, orange terpenes, orcinyl-3 or 3-methoxy-5-methylphenol, oxane ™ or cis-galbanum oxathiane, para cresyl methyl ether or para methyl anisole, patchouli, phenyl ethyl alcohol, phenyl ethyl dimethyl carbinol, polysantol ™ or santol pentenol, prenyl acetate, sauvignone ™ or 5-mercapto-5-methyl-3-hexanone, sclareolate ™ or clary propionate, shisolia, strawberiff ™ or 2-methyl-2-pentenoic acid, terpinolene or 4-isopropylidene-1-methylcyclohexene, tetrahydro muguol ™ or citrus ocimenol, thesaron ™ (1R,6S)-2,2,6-Trimethyl-cyclohexanecarboxylic acid ethyl ester, tobacarol ™ or 5-tetramethyl oxatricyclododecane, undecavertol ™ or violet decenol, verdox ™ or green acetate, verdural B ™ or (Z)-3-hexen-1-yl isobutyrate, violettyne ™ or violet dienyne, violiff ™ or violet methyl carbonate. |
| Neutralize malodors | Suitable malodor neutralizing materials include aldehydes ketones, ionones and mixtures thereof. Specific examples are listed below. Specific aldehydes include the group consisting of: Adoxal ™ (2,6,10-Trimethyl-9-undecenal), Bourgeonal ™ (4-t-butylbenzenepropionaldehyde), Lilestralis 33 ™ (2-methyl-4-t-butylphenyl)propanal), Cinnamic aldehyde, cinnamaldehyde (phenyl propenal, 3-phenyl-2-propenal), Citral, Neral (dimethyloctadienal, 3,7-dimethyl-2,6-octadien-1-al), Cyclal C ™ (2,4-dimethyl-3-cyclohexen-1-carbaldehyde), Florhydral ™ (3-(3-Isopropyl-phenyl)-butyraldehyde), Citronellal (3,7-dimethyl 6-octenal), Cymal (2-methyl-3-(para-isopropylphenyl)propionaldehyde), cyclamen aldehyde, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional ™ (3-(1,3-Benzodioxol-5-yl)-2-methylpropanal); 2-Methyl-3-(3,4-methylenedioxyphenyl)propanal), Intreleven aldehyde (undec-10-en-1-al), Ligustral ™ (2,4-dimethylcyclohex-3-ene-1-carbaldehyde), Trivertal ™ (2,4-dimethyl-3-cyclohexene-1-carboxaldehyde), Jasmorange ™ or satinaldehyde (2-methyl-3-tolylproionaldehyde, 4-dimethylbenzenepropanal), Lyral ™ (4-(4-hydroxy-4-methyl pentyl)-3-cyclohexene-1-carboxaldehyde), Melonal ™ (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde ™ (iso hexenyl tetraydrobenzaldehyde), trifernal ™ ((3-methyl-4-phenyl propanal, 3-phenyl butanal), lilial (3-(4-tert-Butylphenyl)-2-methylpropanal), benzenepropanal (4-tert-butyl-alpha-methyl-hydrocinnamaldehyde), Dupical ™ (muguet butanal), tricyclodecylidenebutanal (4-Tricyclo5210-2,6decylidene-8butanal), |

TABLE 1-continued

| Purpose | Volatile Material |
|---|---|
| | Melafleur ™ (1,2,3,4,5,6,7,8-octahydro-8,8-dimethyl-2-naphthaldehyde), Methyl Octyl Acetaldehyde, aldehyde C-11 MOA (2-mehtyl deca-1-al), Onicidal ™ (2,6,10-trimethyl-5,9-undecadien-1-al), Citronellyl oxyacetaldehyde, Muguet aldehyde 50 ™ (3,7-dimethyl-6-octenyl) oxyacetaldehyde, phenylacetaldehyde, Mefranal ™ (3-methyl-5-phenyl pentanal), dimethyl tetrahydrobenzene aldehyde (2,4-dimethyl-3-cyclohexene-1-carboxaldehyde), 2-phenylproprionaldehyde, Hydrotropaldehyde (2-phenyl propionaldehyde), Canthoxal ™ (para-anisyl propanal), anisylpropanal 4-methoxy-alpha-methyl benzenepropanal (2-anisylidene propanal), Cyclemone A ™ (1,2,3,4,5,6,7,8-octahydro-8,8-dimethyl-2-naphthaldehyde), Precyclemone B ™ (1-cyclohexene-1-carboxaldehyde), and mixtures thereof. Particular examples include the group consisting of: Melonal ™ (2,6-Dimethyl-5-Heptenal), Methoxy Melonal (6-methoxy-2,6-dimethylheptanal), Florhydral ™ (3-(3-Isopropyl-phenyl)-butyraldehyde), and mixtures thereof. Specific ketones include those selected from the group consisting of: iso jasmone, methyl beta naphthyl ketone, musk indanone, tonalid ™ or musk tetralin, alpha-damascone, beta-damascone, delta-damascone, iso-damascone, damascenone, methyl-dihydrojasmonate, menthone, carvone, camphor, fenchone, alpha-ionone, beta-ionone, dihydro-beta-ionone, gamma-methyl ionone, alpha-methyl ionone, n-beta-methyl ionone isomer, fleuramone ™ or 2-heptylcyclopentan-1-one, dihydrojasmone, cis-jasmone, iso-e-super ™ or patchouli ethanone, methyl cedrylketone or methyl cedrylone, acetophenone, methyl-acetophenone, para-methoxy-acetophenone, methyl-beta-naphtyl-ketone, benzyl-acetone, benzophenone, para-hydroxy-phenyl-butanone, celery ketone or livescone ™, 6-isopropyldecahydro-2-naphtone, dimethyl-octenone, freskomenthe ™ or 2-butan-2-ylcyclohexan-1-one, 4-(1-ethoxyvinyl)-3,3,5,5,-tetramethyl-cyclohexanone, methyl-heptenone, 2-(2-(4-methyl-3-cyclohexen-1-yl)propyl)-cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4(5h)-indanone, 4-damascol ™ or pepper hexanone, dulcinyl ™ or4-(1,3-benzodioxol-5-yl)butan-2-one, gelsone ™ or ethyl 2-acetyloctanoate, hexalon ™ or allyl alpha ionone, methyl cyclocitrone ™ or 1-(3,5,6-trimethyl-1-cyclohex-3-enyl)ethanone, methyl-lavender-ketone ™ or 3-(hydroxymethyl)nonan-2-one, orivone ™ or 4-(2-methylbutan-2-yl)cyclohexan-1-one, para-tertiary-butyl-cyclohexanone, verdone ™ or 2-tert-butylcyclohexan-1-one, delphone ™ or 2-pentylcyclopentan-1-one, muscone, neobutenone ™ or 1-(5,5-dimethyl-1-cyclohexenyl)pent-4-en-1-one, plicatone ™ or octahydro-7-methyl-1,4-methanonaphthalen-6(2H)-one, veloutone ™ or 2,2,5-trimethyl-5-pentylcyclopentan-1-one, 2,4,4,7-tetramethyl-oct-6-en-3-one, tetrameran ™ or floral undecenone, hedione ™ or methyl dihydrojasmonate, gamma undecalactone, gamma decalactone, gamma octalactone, ethylene brassylate, pentadecanolide, methyl nonyl ketone, cyclopentadecanone, 3,4,5,6-tetrahydropseudoionone, 8-hexadecenolide, dihydrojasmone, 5-cyclohexadecenone, and mixtures thereof. |

The composition may be formulated such that the composition comprises a volatile material mixture comprising about 10% to about 100%, by total weight, of volatile materials that each having a VP at 25° C. of less than about 0.01 torr; alternatively about 40% to about 100%, by total weight, of volatile materials each having a VP at 25° C. of less than about 0.1 torr; alternatively about 50% to about 100%, by total weight, of volatile materials each having a VP at 25° C. of less than about 0.1 torr; alternatively about 90% to about 100%, by total weight, of volatile materials each having a VP at 25° C. of less than about 0.3 torr. The volatile material mixture may include 0% to about 15%, by total weight, of volatile materials each having a VP at 25° C. of about 0.004 torr to about 0.035 torr; and 0% to about 25%, by total weight, of volatile materials each having a VP at 25° C. of about 0.1 torr to about 0.325 torr; and about 65% to about 100%, by total weight, of volatile materials each having a VP at 25° C. of about 0.035 torr to about 0.1 torr. One source for obtaining the saturation vapor pressure of a volatile material is EPI Suite™, version 4.0, available from U.S. Environmental Protection Agency.

The volatile compositions disclosed herein and used in the cartridge of the present disclosure may be provided in the first and second chambers in liquid form. The volatile compositions may be provided without any solid carrier material and may simply be provided as a liquid solution, suspension, or other mixture within the first and second chambers. This may allow the cartridge of the present disclosure to have an advantageously simple construction.

The present disclosure is illustrated by the below Examples, which are not to be construed as limitative.

EXAMPLES

Example 1

Cartridges were prepared according to Table 2 below. The cartridges used in Inventive 1, Inventive 2, Comparative 2, and Comparative 3 included two separate chambers, one housing fast-evaporating volatile materials (higher vapor pressure) and one housing low-evaporating volatile materials (lower vapor pressure). The cartridge used in Comparative 1 utilised a single chamber containing a single volatile material mixture. Evaporative surface area refers to the surface area through which a volatile material may evaporate from each chamber.

The fast chamber refers to the chamber housing the faster-evaporating volatile material, and the slow chamber refers to the chamber housing the slower-evaporating volatile material.

TABLE 2

| | Inventive 1 | Inventive 2 | Comparative 1 (single chamber) | Comparative 2 | Comparative 3 |
|---|---|---|---|---|---|
| Average vapor pressures at 25° C. (torr) | Fast chamber: 0.23 Slow chamber: 0.05 | Fast chamber: 0.23 Slow chamber: 0.05 | 0.1 | Fast chamber: 0.23 Slow chamber: 0.05 | Fast chamber: 0.23 Slow chamber: 0.05 |
| Volume ratio for fast:slow chamber | 1:1.4 | 1:1.4 | n/a | 1:1.4 | 1:1.4 |
| Ratios of evaporative surface areas (Fast:Slow chambers) | 1:5 | 1:1.7 | n/a (single chamber) | 1:10 | 1:1 |
| Total evaporative surface area | 27 $cm^2$ | 27 $cm^2$ | 27 $cm^2$ | 27 $cm^2$ | 27 $cm^2$ |

The evaporation results of volatile compositions are listed in Table 3.

TABLE 3

| | Cumulative mass evaporated (mg) | | | |
|---|---|---|---|---|
| | Day 1 | Day 3 | Day 7 | Day 15 |
| Inventive 1 | 2.5 | 6.3 | 15.5 | 34.3 |
| Inventive 2 | 1.8 | 5.5 | 12.7 | 29.5 |
| Comparative 1 | 1.7 | 4.2 | 10.4 | 22.6 |
| Comparative 2 | 2.7 | 7 | 17.3 | 38.6 |
| Comparative 3 | 1.4 | 3.7 | 8.9 | 19.4 |

By separating the perfume materials into two chambers where slower evaporating notes are given a bigger evaporation area, the above results are obtained. Table 3 demonstrates that, using the same parent perfume, the two-chamber products Inventive 1 and Inventive 2 provide greater perfume evaporation, specifically greater evaporation of 'bottom' notes, than the single-chamber Comparative 1. This confirms that providing two separate volatile materials allows for an improved evaporation profile, and a broader scent palette.

Table 3 also demonstrates that Inventive 1 and Inventive 2, having a ratio of evaporative surface areas of 1:5 and 1:1.7, respectively, provide improved perfume release as compared to Comparative 3.

Example 2

Table 4 demonstrates that Inventive 1 and Inventive 2 provide a similar or improved scent intensity to the single-chamber Comparative 1.

Table 4 also demonstrates that Inventive 1 and Inventive 2 provide improved scent intensity to Comparative 2, and a better perfume balance (ratio of scent intensity of top:bottom notes) than Comparative 3. Specifically, the scent intensity for Comparative 2 is poor, and the perfume balance for Comparative 3 was unpleasant, resulting in an undesirable smell.

As stated in Example 1, the total evaporative surface area for the fast and slow chambers is 27 $cm^2$.

TABLE 4

| Chamber | Ratio of evaporative surface areas for fast:slow chamber | Perfume Strength [Molar Olfactive Index*] (×10^4) | Initial evaporation rate (mg/h) | Scent intensity in air [Molar Olfactive Index* × perfume concentration in air] (×10^4) / mg/L |
|---|---|---|---|---|
| Inventive example 1 | | | | |
| Fast | 1:5 | 3.6 | 3.4 | 12.24 |
| Slow | | 0.85 | 2.92 | 2.48 |
| Total | | | | 14.72 |
| Inventive example 2 | | | | |
| Fast | 1:1.7 | 3.6 | 5.83 | 20.99 |
| Slow | | 0.85 | 1.52 | 1.29 |
| Total | | | | 22.28 |
| Comparative example 1 | | | | |
| Single chamber | — | 1.6 | 8.51 | 13.62 |
| Comparative example 2 | | | | |
| Fast | 1:10 | 3.6 | 1.89 | 6.8 |
| Slow | | 0.85 | 3.18 | 2.7 |
| Total | | | | 9.51 |

TABLE 4-continued

| Chamber | Ratio of evaporative surface areas for fast:slow chamber | Perfume Strength [Molar Olfactive Index*] (×10^4) | Initial evaporation rate (mg/h) | Scent intensity in air [Molar Olfactive Index* × perfume concentration in air] (×10^4) / mg/L |
|---|---|---|---|---|
| Comparative example 3 | | | | |
| Fast | 1:1 | 3.6 | 10.20 | 36.72 |
| Slow | | 0.85 | 1.75 | 1.49 |
| Total | | | | 38.21 |

*Molar Olfactive Index (MOI) is a relative measure of perfume strength. The perceived scent intensity in the air of a perfume will depend on the perfume strength (i.e. MOI) and the concentration of the perfume in the air, which itself depends on the evaporation rate.

As shown by comparing the results in Tables 3 and 4 of Examples 1 and 2, respectively, Inventive Examples 1 and 2 having a ratio of evaporative surface areas of 1:5 and 1:1.7, respectively, provide an excellent balance between total perfume released into the air (Table 3) and the respective amounts of fast- and slow-evaporating perfumes released. The Comparative Examples 1 to 3 result in either an insufficient release of perfume (poor scent intensity), undesirable relative release rates for the fast- and slow-evaporating perfumes (poor perfume balance), or both.

These results confirm the surprising advantages achieved by using a ratio of evaporative surface areas as disclosed herein.

General Method for Predicting Perfume Strength:

1. *Perfume strength is predicted through a parameter "Molar Olfactive Index" (MOI).

$$MOI = \sum_i \frac{x_i \cdot P^{sat}_{vap,i}}{ODT_i}$$

ODT—Odor detection threshold of component, x—mole fraction, $$P^{vap}_{sat,i}$$

Saturation Vapor pressure

2. Concentration of perfume in air is calculated using evaporation rate of perfume in target space with accounting for dilution due to air changes per hour.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm.".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any example disclosed or claimed herein or that it alone, or in any combination with any other reference or references, teaches, suggests or discloses any such example. Further, to the extent that any meaning or definition of a term in this document conflicts with any meaning or definition of the same term in a document incorporated by reference, the meaning or definition assigned to that term in this document shall govern.

While particular examples of the present disclosure have been illustrated and described, it would be obvious to those skilled in the art that various other changes and modifications could be made without departing from the spirit and scope of the present disclosure. It is therefore intended to cover in the appended claims all such changes and modifications that are within the scope of the present disclosure.

What is claimed is:

1. A cartridge for a volatile composition dispenser, comprising:

(a) a first chamber comprising a first chamber opening and containing a first volatile composition;

(b) a second chamber comprising a second chamber opening and containing a second volatile composition, where the second chamber is fluidly isolated from the first chamber;

(c) a first breathable membrane covering the first chamber opening and having a first evaporation region through which the first volatile composition can evaporate; and (d) a second breathable membrane covering the second chamber opening and having a second evaporation region through which the second volatile composition can evaporate;

wherein a ratio between a surface area of the first evaporation region to a surface area of the second evaporation region is in a range of 1:1.3 to 1:6.

2. The cartridge according to claim 1, wherein the first evaporation region is fluidly isolated from the second evaporation region.

3. The cartridge according to claim 2, wherein:

the cartridge comprises a sealing region fluidly isolating the first and second evaporation regions from each other; and the sealing region comprises:

an impermeable material; or a gap between the first and second evaporation regions.

4. The cartridge according to claim 1, wherein an evaporation rate of the first volatile composition at standard temperature and pressure is higher than an evaporation rate of the second volatile composition at standard temperature and pressure.

5. The cartridge according to claim 1, wherein a ratio between a surface area of the first evaporation region and a surface area of the second evaporation region is in a range of 1:1.4 to 1:5.

6. The cartridge according to claim 1, wherein a ratio between a volume of the first chamber and a volume of the second chamber is in a range of 1:1 to 1:6.

7. The cartridge according to claim 1, wherein a ratio between a surface area of the first chamber opening and a surface area of the second chamber opening is in a range of 1:1.3 to 1:6.

8. The cartridge according to claim 1, wherein a top portion of the first chamber is substantially coplanar with a top portion of the second chamber, and/or a bottom portion of the first chamber is substantially coplanar with a bottom portion of the second chamber.

9. The cartridge according to claim 1, wherein the first chamber is arranged side by side with the second chamber.

10. The cartridge according to claim 1, wherein:

the first chamber opening is substantially coplanar with the second chamber opening; and/or the first breathable membrane is substantially coplanar with the second breathable membrane; and/or the first evaporation region is substantially coplanar with the second evaporation region.

11. The cartridge according to claim 1, wherein:

the first chamber is partially surrounded by the second chamber (e.g. in two dimensions), or the second chamber is partially surrounded by the first chamber (e.g. in two dimensions).

12. The cartridge according to claim 1, comprising a first rupturable impermeable substrate disposed over the first chamber opening and a second rupturable impermeable substrate disposed over the second chamber opening, wherein:

when in an unruptured state the first and second rupturable impermeable substrates prevent evaporation of the first volatile composition and second volatile composition; and when in a ruptured state the rupturable impermeable substrates allow evaporation of the first volatile composition and second volatile composition.

13. The cartridge according to claim 12, wherein:

when in an unruptured state the first and second rupturable impermeable substrates prevent contact of the first and second volatile compositions with the first and second breathable membranes, respectively; and when in a ruptured state the first and second rupturable impermeable substrates allow contact of the first and second volatile compositions with the first and second breathable membranes, respectively.

14. The cartridge according to claim 13, comprising a rupture mechanism configured to, upon activation, cause rupture of the first and second rupturable impermeable substrates, wherein the rupture mechanism is configured to, upon activation, cause simultaneous rupture of the first and second rupturable impermeable substrates.

15. The cartridge according to claim 14, wherein the rupture mechanism is sandwiched between the first and second rupturable impermeable substrates and the first and second breathable membranes.

16. The cartridge according to claim 12, wherein the rupture mechanism comprises at least a first rupture element configured to pierce the first rupturable impermeable substrate and a second rupture element configured to pierce the second rupturable impermeable substrate.

17. The cartridge according to claim 1, wherein the first and second volatile compositions are liquid compositions.

18. The cartridge according to claim 1, wherein the first and second breathable membranes are constructed from the same material.

19. A volatile composition dispenser, comprising:

a cartridge according to claim 1; and a housing defining an interior compartment within which the cartridge is disposed.

20. The volatile composition dispenser according to claim 19, further comprising an activation member disposed on the housing, wherein actuation of the activation member allows simultaneous evaporation of the first volatile composition from the first chamber through the first evaporation region of the breathable membrane and the second volatile composition from the second chamber through the second evaporation region of the breathable membrane.

* * * * *